United States Patent
Schaller et al.

(10) Patent No.: US 7,251,845 B2
(45) Date of Patent: Aug. 7, 2007

(54) PATIENT BED, AND METHOD FOR REPRODUCIBLY POSITIONING AND SUPPORTING A PATIENT THEREWITH

(75) Inventors: Stefan Schaller, Fürth (DE); Jürgen Simon, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 113 days.

(21) Appl. No.: 11/121,574

(22) Filed: May 4, 2005

(65) Prior Publication Data
US 2005/0251914 A1    Nov. 17, 2005

(30) Foreign Application Priority Data
May 4, 2004    (DE)    ............ 10 2004 021 972

(51) Int. Cl.
*A61G 7/015* (2006.01)
(52) U.S. Cl. ............... 5/613; 5/616; 5/731; 5/935
(58) Field of Classification Search ............ 5/613, 5/615, 616, 713, 715, 731, 733, 734, 935
See application file for complete search history.

(56) References Cited

U.S. PATENT DOCUMENTS

| | | | | |
|---|---|---|---|---|
| 4,542,547 A | * | 9/1985 | Sato | 5/713 |
| 4,989,283 A | * | 2/1991 | Krouskop | 5/713 |
| 5,446,933 A | * | 9/1995 | Gabelhouse | 5/670 |
| 6,108,843 A | * | 8/2000 | Suzuki et al. | 5/713 |
| 6,721,981 B1 | * | 4/2004 | Greenhalgh et al. | 5/716 |
| 6,829,797 B2 | * | 12/2004 | Partian | 5/713 |
| 7,069,610 B1 | * | 7/2006 | Chai | 5/731 |
| 2003/0225325 A1 | | 12/2003 | Kagermeier et al. | |

FOREIGN PATENT DOCUMENTS

DE    30 16 387    11/1981

* cited by examiner

*Primary Examiner*—Michael Trettel
(74) *Attorney, Agent, or Firm*—Schiff Hardin LLP

(57) ABSTRACT

A patient bed and a method for reproducibly positioning and supporting a patient in a medical diagnosis or therapy apparatus, such as a CT apparatus or an MRI apparatus, involve supporting at least regions of the patient body in a desired position on the patient bed and using at least one positioning unit to position the regions of the patient body relative to the patient bed. The patient bed has a number of height-adjustable elements arranged like a matrix that are individually adjustable in terms of height.

28 Claims, 3 Drawing Sheets

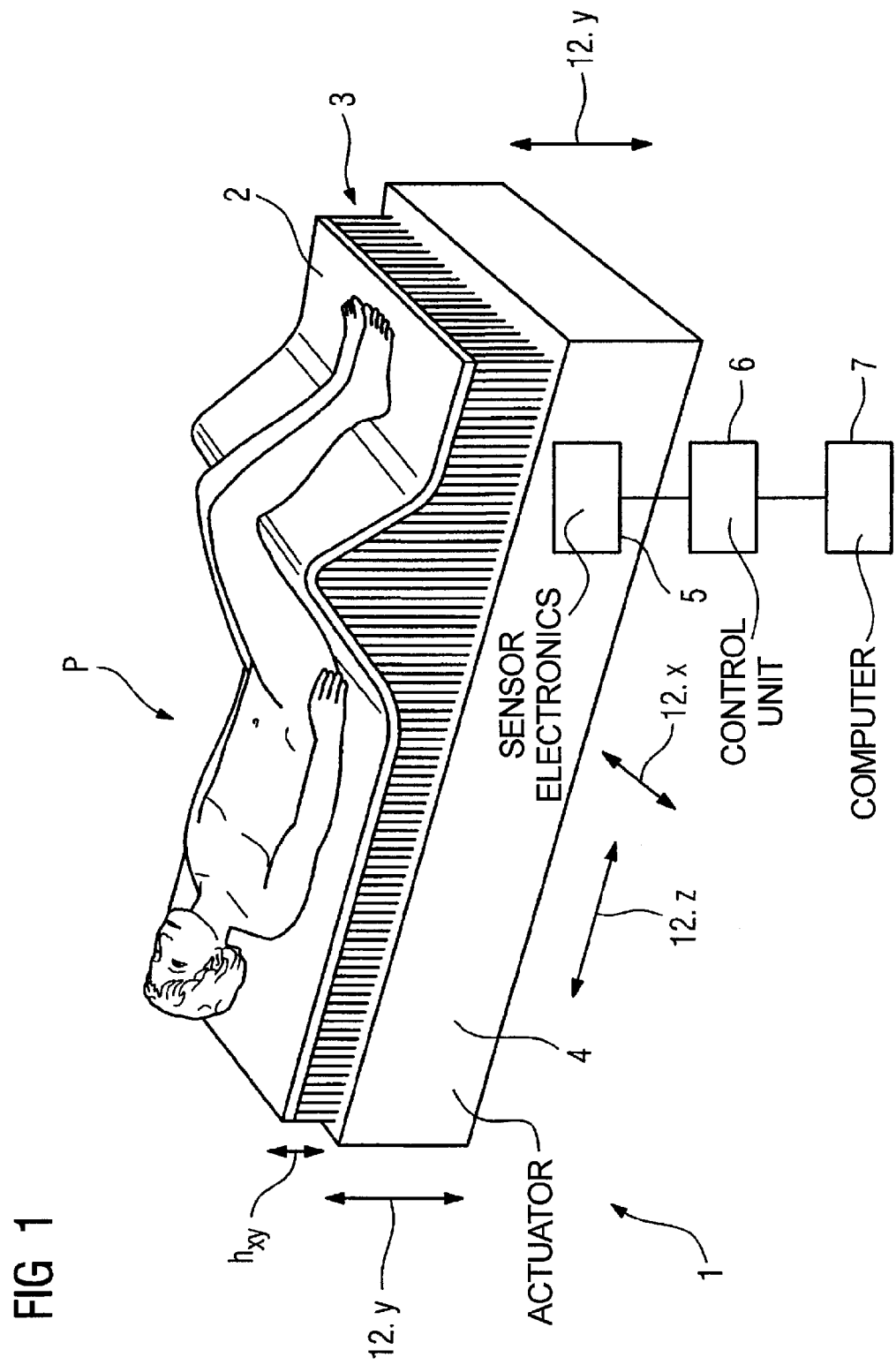

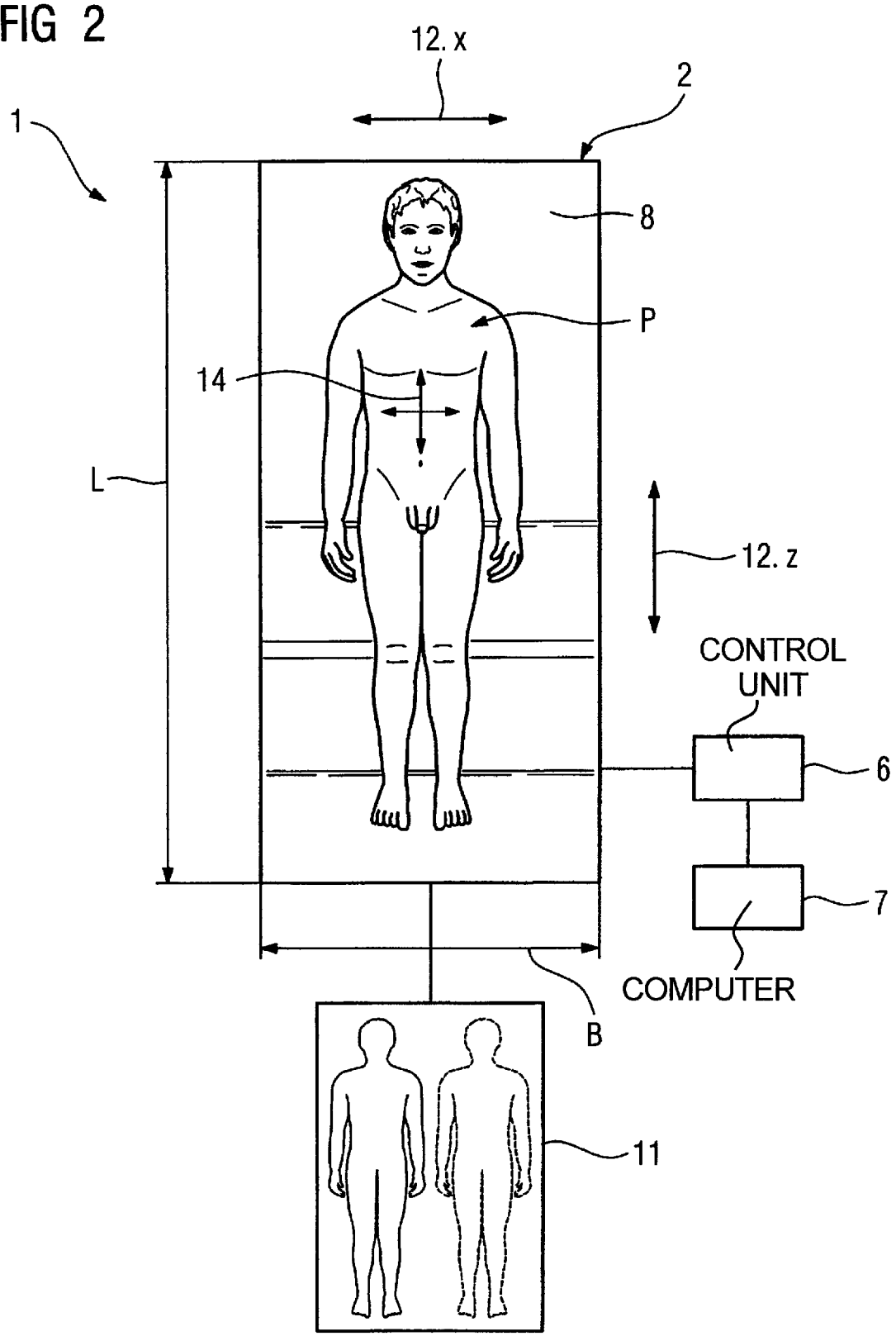

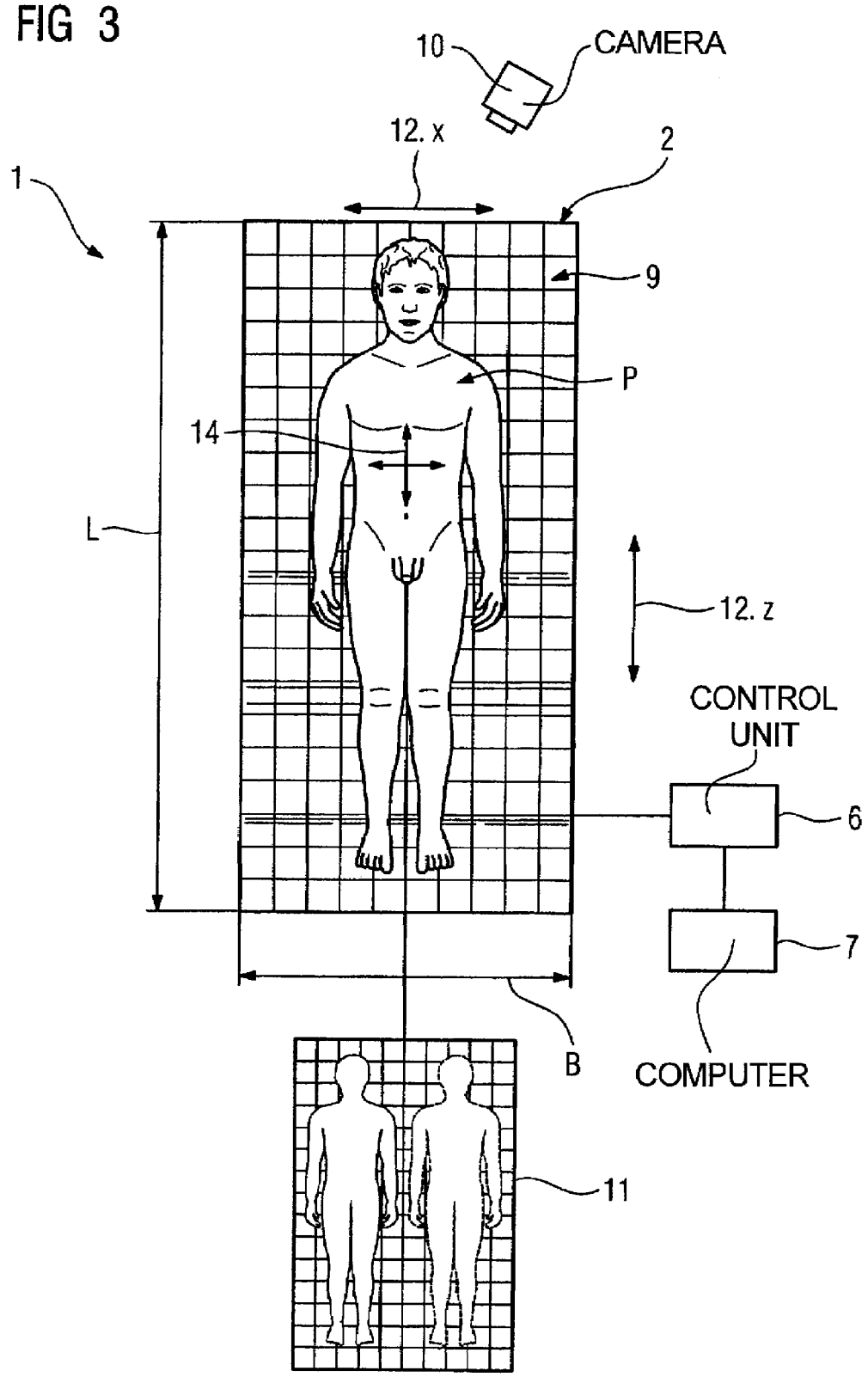

PATIENT BED, AND METHOD FOR REPRODUCIBLY POSITIONING AND SUPPORTING A PATIENT THEREWITH

BACKGROUND OF THE INVENTION

1. Field of the Invention

The present invention concerns a patient bed for reproducibly positioning and supporting a patient in a medical diagnosis or therapy apparatus, preferably in a CT apparatus or in an MRI apparatus (magnetic resonance imaging apparatus), of the type wherein the patient bed supports at least some regions of the patient body in a desired position and at least one positioning means enables positioning of the regions of the body with regard to the patient bed.

The invention also concerns a method for reproducibly positioning and supporting a patient in a medical diagnosis or therapy apparatus, preferably in a CT apparatus or in an MRI apparatus, wherein at least some regions of the patient body are supported in a desired position, and wherein at least some regions of the patient body are positioned with regard to the patient bed.

2. Description of the Prior Art

In various medical applications, it is necessary to support and position a patient exactly as he or she was supported and positioned in a preceding examination or treatment. For example, in radiation therapy that follows a computed tomography examination, it is particularly important that the patient be supported and positioned precisely as he or she was supported and positioned in the preceding computed tomography examination. Various special supporting and positioning aids are used for this purpose.

One such positioning aid described in European Application 03004035, the teachings of which are incorporated herein by reference. A method and a device for repeated precise relative positioning of a patient are specified in this document. In this method and with this device, a first reference position of a patient is acquired with two cameras that preferably image the patient from two independent planes. If the patient should again be brought into the original first position, the current position of the patient is reacquired by the cameras and compared with the exposures of the first reference position. The current position of the patients is modified until the camera images of the current position coincide with the camera images of the first reference position. A repeated and very precise positioning of a patient is thereby enabled. However, it is sometimes possible that this desired therapy or examination position of the patient is not comfortable for the patient and therefore cannot be maintained over a longer time span. In order to support the position of a patient or to be able to approximately fix the posture of the patient, various supporting aids are known.

The following supporting aids have previously been used dependent on the body parts of the patient. Skull shells or face masks are attached on the head of the patient for fixing of the head. Specially-formed pads are used for the abdomen. The achievable reproducibility in the repositioning is in the range of a precision of several millimeters to several centimeters. Moreover, these known supporting aids are for the most part considered to be unpleasant and uncomfortable by the patient. Products known as a vacuum mattresses would also be suitable for comfortably maintaining the patient in a fixed position. These are plastic shells that are filled with polystyrene pellets. Upon placement of a patient therein, however, such mattresses can initially shift against one another and, due to body weight, the patient sinks somewhat into the mattress; the air is then suctioned from the plastic shell. When the negative pressure is then taken away again, the mattress loses its shape. In order to keep the shape reproducible, a vacuum mattress must be stored with maintained vacuum for ever patient. In radiation therapy clinics, many hundreds of patients are simultaneously in treatment at a specific point in time, such that this practice is impractical.

For examinations and treatments of the body or body parts, it would be desirable to be able to reproducibly support or fix the patient or parts of the patient's body during the examination or treatment without giving the patient a claustrophobic feeling. Moreover, the examination or fixing of the body part or of the entire body should ensue such that the position can be maintained over a longer time span without the patient developing symptoms of fatigue.

SUMMARY OF THE INVENTION

It is an object of the invention to provide a patient bed and a method for reproducible positioning and supporting a patient that allow repeated, precise supporting and positioning of a patient in a desired position with the patient being comfortably supported or fixed in this position.

The invention proceeds from the recognition that conventional patient beds, for example in a computed tomography apparatus, are for the most part fashioned flat. This flat execution of the patient bed is only roughly suitable for adaptation to the contour of the human body or to the contour of specific body regions. If, for example, the legs or arms of a patient on the patient bed are angled, these body parts are no longer supported by the patient bed.

The invention also proceeds from the recognition that it is possible to comfortably support at least regions of the patient by a patient bed that exhibits an adaptable and variable contour. If the contour of the patient bed and the support of the patient on the patient bed are detected and stored in a first treatment/examination, in a new treatment/examination the patient can, by reproduction of the original patient bed contour and original patient support, be positioned on the patient bed in the same position as the patient was positioned for the first treatment/examination.

Based on these recognitions, the above object is achieved in accordance with the invention by a patient bed for reproducibly positioning and supporting a patient in a medical diagnosis or therapy apparatus, preferably in a CT apparatus or in an MRI apparatus, wherein the patient bed supports at least regions of the patients body in a desired position and includes at least one positioning unit that enables positioning of the regions of the patient body with regard to the patient bed, and wherein the patient bed has a number of height-adjustable elements arranged like a matrix that are individually height-adjustable.

A patient bed is thereby provided that can be three-dimensionally adjusted with regard to the contour of the bed surface. Individual body regions or the entire body of a patient thus can be comfortably supported in a desired position. The more height adjustment elements that are used, the smaller their diameter, and the closer the height adjustment elements are next to one another, the more finely can the structure of a specific surface contour be formed. The height-adjustable elements, for example, can exhibit a round, triangular or rectangular cross-section, and the height-adjustable elements can be arranged back to back or next to one another in series, or offset from one another. The patient can be positioned on the patient bed by the positioning unit. Primarily for repeated examinations/treatments, a reproducible positioning of the patient bed is enabled by the positioning means, and at the same time a comfortable supporting of the patient is enabled by the design of the patient bed.

In an embodiment of the patient bed, at least some of the height-adjustable elements can be formed by height-adjustable support pegs. These support pegs can be executed similar to the elements of a nail board, but in contrast to a nail board of each individual support peg is adjustable in height. For example, each individual support peg can be extractable and retractable like a telescope. In this particular embodiment, it is not necessary for the dimensions of the patient to be enlarged.

For height adjustment of the support pegs, at least one electrical and/or pneumatic and/or hydraulic actuator is provided. If a large number of support pegs are arranged on the patient bed, height adjustment can be effected that is faster relative to a manual setting of the height of each individual support peg. Each individual support peg can have its own actuator for height adjustment.

As an alternative or expansion to the embodiment of the height adjustment elements as support pegs, at least some of the height adjustment elements can be formed from a number of chambers with a flexible wall that are filled (independently of one another) with a (gaseous or liquid) medium. Via the pressure and the filling quantity of the individual chambers, their height can be adjusted. Filling the chambers with a fluid, for example water, enables a simultaneous temperature of setting the patient bed by the temperature of the water. For example, an adaptation to pressure-sensitive body regions can be effected by a combination of height adjustment elements formed by support pegs and height adjustment elements having chambers. The filled chambers are felt to be as soft and comfortable as an air mattress. The embodiment of the height adjustment elements as support pegs can be more suitable for other body parts or examination/treatment requirements.

At least five height adjustment elements should be arranged in series or offset from one another along the width and the length of the patient bed.

In an embodiment of the patient bed, at least one mat is arranged between the patient and the support pegs and/or chambers. A comfortable bed surface thus is achieved for the patient, by (for example) local pressure points (due to individual support pegs and/or chambers) being prevented.

It is advantageous when the individual support pegs and/or individual chambers have a sensor that preferably measures the load pressure on the support peg and/or the pressure in the chamber. Given a patient located on the patient bed, the support pegs and/or the chambers are loaded with different forces by body parts of the patient due to the patient weight and the weight distribution on the patient bed. A specific load/support pattern of the support pegs and/or the chambers results for a specific support or position of the patient. This load/support pattern can be used for repositioning of the patient. Thus, for example, support pegs and/or chambers on which the patient does not lie in a first treatment/examination session and that consequently exhibit a load pressure or a support pressure of zero have the same load pressure or the same support pressure in the case of a subsequent support of the patient. The load/pressure values of the loaded support pegs/chambers analogously should exhibit the same value as in a former treatment/examination. A reproducible positioning using the height adjustment elements can also ensue in the embodiment of the height adjustment elements with sensors.

The sensor can be, for example, a pressure sensor, preferably a piezoelectric pressure sensor. Piezoelectric sensors can detect very slight pressures and pressure differences. Other sensors that are also suitable for force and pressure measurement, however, can be used in the height adjustment elements.

In an embodiment of the patient bed, a control device is provided that controls the adjustment of the height of the support pegs and/or the filling quantity and/or the pressure in the chambers. A more precise, as well as a faster adaptation of the height adjustment elements (and thus of the patient bed contour) is achieved in comparison to manual adjustment of these values.

In a further variant of the patient bed, at least one further sensor (preferably an optical and/or an ultrasound sensor) is used that determines the height of the support pegs. This further sensor can be used to confirm that each peg is at the intended height. Theoretically, a precision of the height adjustment of the support peg in the range of the wavelength of the light that is used can be achieved with such an optical sensor, for example a laser distance sensor.

In the embodiment of the height adjustment elements as individual chambers, a controllable valve that regulates the filling quantity and/or the pressure in each chamber can be provided for each chamber.

Furthermore, a storage arrangement, for example a computer with a fixed disc, can be provided to store the adjustment values of the magnitude of the support pressure of the support pegs, and the filling pressure and the filling quantity of the filling medium in the chambers given a reclining patient. If the adjustment values for adjusted height, filling pressure and filling quantity of the filling medium in the chambers are stored for all support pegs and for all chambers, a specific contour of a patient bed (and thus a specific support of a patient) is stored.

The patient bed and/or the mat between the patient and the height adjustment elements can exhibits a visible grid pattern. At least one camera can be arranged to acquire the position of the patient with regard to the grid pattern is a particularly simple and fast repositioning of a patient on the patient bed can occur.

Corresponding to the device for reproducibly positioning and supporting a patient, in a method for reproducibly positioning and supporting of a patient on a patient bed in a medical diagnosis or therapy apparatus (preferably in a CT apparatus or an MRI apparatus) according to the invention, at least some regions of the patient body are supported in a desired position, and at least some regions of the patient body are positioned with a positioning unit with regard to the patient bed, by at least some regions of the patient body being supported at a number of body locations by a number of individually-adjustable height adjustment elements.

Using the inventive method, individual body regions or the entire body of a patient can be comfortable supported in a desired position. Particularly for examinations/treatments that should be repeated multiple times, a reproducible positioning of a patient and simultaneously a reproducible support of the patient are enabled.

The inventive method can include measuring the load pressure of the height adjustment elements for a reclining patient, and storing the force values of each height adjustment element are stored. The load pressure on the individual height adjustment elements is dependent on the weight of the patient and the support of the patient on the patient bed. If all load pressures on each of the support pegs are known, a fairly exact repositioning of a patient on a patient bed can occur.

By determining and storing the height of each height adjustment element the patient bed, the three-dimensional contour of the patient bed (which corresponds to a specific bearing and position of a patient) can be stored.

In the method, the support and the position of a patient can be adjusted for repositioning until the values of the load pressures of the height adjustment elements and/or the values of the height of each height adjustment element coincide with the stored values.

The method can include acquiring the position of a patient on the patient bed with at least one camera and storing at least one such camera image. For example, two positions of a patient on a patient bed can be brought into agreement, by adjusting the current position of the patient until the respective image of the new position coincides with the stored image of the old position. Such an image comparison can be implemented, for example, by an image-processing algorithm in which a pixel-by-pixel addition or subtraction of the old and the new images occurs.

As an alternative or addition, for repositioning the position of the patient bed and/or the height of the height adjustment elements can be varied with a reclining patient until the current support of the patient coincides with a previously obtained support of the patient.

In the inventive method, a simple repositioning of a patient can ensue with the positioning unit, the camera and a grid pattern on the patient bed, by the support and the position of the patient being adjusted until a currently acquired camera image coincides with a stored camera image of the same patient.

In the inventive method, a comparison of the stored values of the load pressure, the height and the acquired camera images with stored values and images can be implemented and correction suggestions for the support and the position of the patient can be calculated using the differences of the values and the images. For the user of the method, which preferably is used in the field of medical diagnosis or therapy apparatuses, a repositioning of a patient is significantly simplified because the user can effect a rearrangement/repositioning of the entire patient or only specific body parties using the calculated correction suggestions, supported by optical signals or acoustic commands.

Further features of the invention result from the subsequent specification of the exemplary embodiments with reference to the drawings.

DESCRIPTION OF THE DRAWINGS

In the following, the invention is described in detail using preferred exemplary embodiments with the aid of Figures. Only the elements significant for the invention are shown in Figures.

FIG. 1 is a side view of a patient bed with height-adjustable support pegs in accordance with the invention.

FIG. 2 is plan view of the patient bed of FIG. 1.

FIG. 3 is a plan view of a further embodiment of a patient bed with position control in accordance with the invention.

DESCRIPTION OF THE PREFERRED EMBODIMENTS

FIG. 1 shows a patient bed 1 in a side view. The patient bed 1 can be used in a computed tomography apparatus as well as in other medical diagnosis or therapy apparatuses (for example also as an operating table) in which a reproducible support of a patient P or of another examination or treatment subject is necessary. The patient bed 1 has an actuator 4 in the lower region and support pegs 3 disposed above the actuator 4. Each of the support pegs 3 can be individually adjusted in height $h_{xy}$ by the actuator 4. A mat 2 that prevents pressure marks of the support pegs 3 on the body of the patient P is disposed on the support pegs 3. In order to be able to detect the load pressures and the set heights $h_{xy}$ of the support pegs 3, the support pegs 3 are equipped with sensors (shown in FIG. 1) the outputs of which are acquired by sensor electronics 5. A control unit 6 regulates and controls the actuator 4 and accesses the data of the sensor electronics 5. Data for the patient P, namely measurement values such as, for example, the load pressures and the set support peg heights can be stored and evaluated by a computer 7 with memory capacity.

In order to support the patient P in a position that is comfortable and simultaneously advantageous for the medical application, the method can proceed as follows.

The support pegs 3 each are extended to a uniform heights h with the actuator 4. The patient lies on the mat 2 of the patient bed 1. The patient P or an assistant pushes individual body parts, for example arms or legs, into a position that is comfortable for the patient P or advantageous for the measurement. The pressure or the force exerted by the patient P or by the assistant on specific support pegs 3 can be measured by the sensors. The support pegs 3 are lowered in height until the patient P or the assistant exerts no further pressure beyond the pressure of the body weight. The support pegs 3 subsequently can be fixed in their respective heights, whereby the support of the patient P is approximately fixed. It is also possible that the patient's own weight will exert a sufficient pressure on the support pegs 3.

As an alternative to pushing the support pegs 3, all support pegs 3 can be initially in a retracted state. The patient P lies on the mat 2 of the patient bed 1 and assumes a posture advantageous for the examination or treatment or comfortable for the patient P. The support pegs 2 located underneath the patient P are extended in height $h_{xy}$ until the sensors of the support pegs 3 detect a resistance by, for example, body parts of the patient P. The support pegs 3 are subsequently held at this height.

For example, in FIG. 1 can be seen that support pegs 3 in the calf region and in the rear thigh region support the legs in the region of the angled legs of the patient P. This leg position can be maintained a longer time by the patient P than without such support.

The support assumed by the patient P in a first treatment or examination can be archived by storage of the values (such as support peg height and load pressure) in the memory of the computer 7. If a further treatment or examination should subsequently occurs with the same patient P on the same bed as for the first treatment, the original patient bed position can be set with the actuator 4 and the measurement data of the computer 7 before the patient P reclines.

In order to simplify the support and rearrangement of the patient, the patient bed 1 can have a movement mechanism (not shown in the figures) that enables the patient bed to tilt, to rotate and to vary in terms of height and to move linearly. The movement possibilities of the patient bed 1 are symbolized by the double arrows with reference characters 12.x, 12.y and 12.z. Tilt and rotation movements of the patient bed are also possible by different raising/lowering of the head and foot of the patient bed.

FIG. 2 shows a plan view of the patient bed 1 of FIG. 1. The support surface of the patient bed 1 with width B and length L can be seen as well as the silhouette of the patient P lying on the mat 2. In this view, it is also easily seen that a region 8 in which the support pegs are not loaded by the weight of the patient P exists around the patient P. This region 8 can be used for a repositioning of the patient P. As already described with FIG. 1, all data can be archived in the memory of the computer 7. If a current position of a patient P should be brought into agreement with a previously assumed position, it is thus advantageous to bring the region 8 (the loaded support pegs) into congruence in the previous and the current positions. In order to simplify the repositioning, optical and/or acoustic commands or signals can be output via a correction display and the patient P can be rearranged corresponding to these signals via patient movement indicated by the arrows 14 until the current position of the patient P coincides with the desired position. In this embodiment of the correction display 11, the "real position" of the patient P is represented by the silhouette with continuous outline. The desired "desired position" is represented by the silhouette with a dashed outline.

As an alternative to patient movement 14 the patient bed 1, the position of the patient bed 1 itself can be changed by movement of the patient bed in the x-direction, z-direction or tilting/rotation of the patient bed 1 and variation of the height hxy of the height adjustment elements until the current bearing of the patient P coincides with a previously-assumed bearing of the patient P.

A further possibility for repositioning of the patient P on the patient bed 1 is explained in FIG. 3. The mat 2 of the patient bed 1 and the patient P are shown in plan view. A grid pattern 9 is visible on the mat 2, here in the form of a rectangular grid. The position of the patient P on the patient bed 1 is established by at least one image with a camera 10. When the patient P reclines on the patient bed 1 in a new examination, the position of the patient P is established with at least one image. A position correction can be calculated by the computer 7 via the differences of the uncovered and covered squares of the grid arrangement 9 in the current image relative to the previous image of the first examination.

As explained in connection with the three figures, a reproducible supporting of the patient P is accomplished using the support pegs 3. A positioning and/or repositioning of the patient P for the examination/treatment can ensue using the support pegs 3 with their sensors and other auxiliary means (such as cameras, optical markers) or by a movement of the patient bed 1 with the reclining patient.

Overall, a patient bed and method for reproducible positioning and support of a patient that allows a repeated, precise bearing and positioning of a patient in a desired position and that allows the patient to be at least supported or fixed comfortably in this position is provided.

Although modifications and changes may be suggested by those skilled in the art, it is the intention of the inventors to embody within the patent warranted hereon all changes and modifications as reasonably and properly come within the scope of their contribution to the art.

We claim as our invention:

1. A patient bed configured to receive a patient thereon for reproducibly positioning and supporting the patient, said patient bed comprising:
    a bed base; and
    a plurality of height-adjustable elements comprising support pegs disposed matrix-like on said bed base, each of said height-adjustable elements being individually adjustable in height relative to said bed base; and
    a positioning arrangement that interacts with said plurality of height-adjustable elements to selectively adjust the respective heights of individual ones of said height-adjustable elements to selectively position a region of the patient relative to the bed base.

2. A patient bed as claimed in claim 1 wherein said positioning arrangement comprises, for each of said height-adjustable support pegs, an actuator selected from the group consisting of electrical actuators, pneumatic actuators and hydraulic actuators.

3. A patient bed as claimed in claim 2 wherein each of said plurality of height-adjustable support pegs comprises a sensor that measures a load pressure on that height-adjustable support peg.

4. A patient bed as claimed in claim 3 wherein each sensor is a pressure sensor.

5. A patient bed as claimed in claim 3 wherein said positioning arrangement includes a control unit that controls adjustment of the respective heights of the individual support pegs dependent on the respective load pressures measured by the respective sensors.

6. A patient bed as claimed in claim 5 comprising a further sensor, selected from the group consisting of optical sensors and ultrasound sensors, that determines the respective heights of the respective support pegs and supplies a signal to said control device to confirm that each support peg is at an intended height.

7. A patient bed as claimed in claim 5 comprising a computer with a memory wherein, for an individual patient reclining on said patient bed, respective adjustment values for said support pegs are stored, including the load pressure for each of said support pegs.

8. A patient bed as claimed in claim 1 wherein said plurality of height-adjustable elements also comprises a plurality of individually height-adjustable elements each having a chamber with a flexible wall, and wherein said positioning arrangement fills the respective chambers with fluid independently of each other to adjust the respective heights of the respective height-adjustable elements.

9. A patient bed as claimed in claim 8 wherein each of said chambers has a sensor that measures a pressure of said fluid in that chamber.

10. A patient bed as claimed in claim 9 wherein said positioning arrangement comprises, for each of said chambers, a controllable valve that regulates filling of that chamber with said fluid dependent on the pressure measured by the sensor for that chamber.

11. A patient bed as claimed in claim 10 wherein said positioning arrangement comprises a control device connected to each of said controllable valves for controlling filling of the respective chambers with said fluid.

12. A patient bed as claimed in claim 11 comprising a further sensor, selected from the group consisting of optical sensors and ultrasound sensors, that determines the respective heights of the respective height-adjustable elements and supplies a signal to said support unit to confirm that each of said height-adjustable elements is at an intended height.

13. A patient bed as claimed in claim 11 wherein said positioning arrangement comprises a computer with a memory in which, for an individual patient reclining on the patient bed, respective adjustment values for filling each of said chambers with said fluid is stored, together with the filling pressure.

14. A patient bed as claimed in claim 1 wherein said bed base has a width and a length, and wherein said plurality of height-adjustable elements comprises at least five height-adjustable elements disposed in succession along said width and at least five height-adjustable elements disposed in succession along said length.

15. A patient bed as claimed in claim 14 wherein said height-adjustable elements disposed along at least one of said width or said length are disposed in a substantially linear series.

16. A patient bed as claimed in claim 14 wherein said height-adjustable elements disposed along at least one of said width or said length are disposed offset relative to each other.

17. A patient bed as claimed in claim 1 comprising a mat disposed over said plurality of height-adjustable elements, said mat being adapted to receive said patient thereon.

18. A patient bed as claimed in claim 17 wherein said mat has a visible grid pattern thereon, and comprising a camera disposed to acquire an image of the patient on the mat relative to said grid pattern, and an image processor supplied with said image for allowing reproducible positioning of the patient with respective to said grid pattern.

19. A patient bed as claimed in claim 1 wherein said bed base has a visible grid pattern thereon, and comprising a camera disposed to acquire an image of the patient on the bed base relative to said grid pattern, and an image processor supplied with said image for allowing reproducible positioning of the patient with respective to said grid pattern.

20. A method for reproducibly positioning and supporting a patient on a patient bed comprising the steps of:
   disposing a patient on a patient bed and supporting said patient on said patient bed at multiple body locations of the patient with a plurality of individually height-adjustable elements; and
   positioning a region of the patient on the patient bed by individually adjusting the respective heights of the height-adjustable elements; and
   obtaining an image of a patient on the patient bed with a camera and storing said image and using said image to reposition that patient on the patient bed at a time after said image is obtained and stored.

21. A method as claimed in claim 20 comprising measuring a load pressure produced by the patient on each of the height-adjustable elements, and storing respective load pressure values for the respective height-adjustable elements for an individual patient.

22. A method as claimed in claim 21 comprising, for repositioning said individual patient on said patient bed, placing said individual patient on said patient bed at a time after said load pressure is measured, and respectively automatically positioning said individual height-adjustable elements until the respective load pressures of the individual height-adjustable elements coincide with the previously measured load pressures.

23. A method as claimed in claim 22 comprising automatically electronically generating and displaying position correction proposals, selected from the group consisting of optically displayed information and acoustically emitted information, dependent on a difference between said respective load pressures and said measured load pressures.

24. A method as claimed in claim 20 comprising measuring a height produced by the patient on each of the height-adjustable elements, and storing respective height values for the respective height-adjustable elements for an individual patient.

25. A method as claimed in claim 24 comprising, for repositioning said individual patient on said patient bed, placing said individual patient on said patient bed at a time after said height is measured, and respectively automatically positioning said individual height-adjustable elements until the respective heights of the individual height-adjustable elements coincide with the previously measured heights.

26. A method as claimed in claim 25 comprising automatically electronically generating and displaying position correction proposals, selected from the group consisting of optically displayed information and acoustically emitted information, dependent on a difference between said respective heights and said previously measured heights.

27. A method as claimed in claim 20 comprising repositioning said patient on said patient bed at said time after said image is obtained and stored by obtaining a current image of the patient on the patient bed with said camera and adjusting the position of the patient on the patient bed until said stored image and said current image coincide.

28. A method as claimed in claim 27 comprising automatically electronically generating and displaying position correction proposals, selected from the group consisting of optically displayed information and acoustically emitted information, dependent on a difference between said stored image and said current image.

* * * * *